(12) United States Patent
Kim et al.

(10) Patent No.: US 8,597,897 B2
(45) Date of Patent: Dec. 3, 2013

(54) METHOD OF RAPIDLY DETECTING MICROORGANISMS USING NANOPARTICLES

(75) Inventors: Min Gon Kim, Daejeon (KR); Yong Beom Shin, Daejeon (KR); Yoon Joo Sung, Gyeongsangbuk-do (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 13/511,574

(22) PCT Filed: Nov. 24, 2010

(86) PCT No.: PCT/KR2010/008356
§ 371 (c)(1),
(2), (4) Date: Sep. 14, 2012

(87) PCT Pub. No.: WO2011/065747
PCT Pub. Date: Jun. 3, 2011

(65) Prior Publication Data
US 2013/0065220 A1   Mar. 14, 2013

(30) Foreign Application Priority Data
Nov. 24, 2009 (KR) .................. 10-2009-0114138

(51) Int. Cl.
*G01N 33/53* (2006.01)
*G01N 33/554* (2006.01)
*G01N 33/567* (2006.01)

(52) U.S. Cl.
USPC ............ 435/7.1; 435/7.2; 435/7.32; 435/810

(58) Field of Classification Search
None
See application file for complete search history.

(56) References Cited

U.S. PATENT DOCUMENTS

2007/0114181 A1   5/2007   Li et al.
2008/0032420 A1   2/2008   Lambert et al.

FOREIGN PATENT DOCUMENTS

KR   1020020091628   12/2002

OTHER PUBLICATIONS

Korean Office Action, Jun. 18, 2012.
Ninet, B., et al.; "Assessment of Accuprobe *Listeria monocytogenes* Culture Identification Reagent Kit for Rapid Colony Confirmation and Its Application in Various Enrichment Broths," Applied and Environmental Microbiology, 1992, pp. 4055-4059, vol. 58.
Lynch, MJ, et al.; "Evaluation of an automated immunomagnetic separation method for the rapid detection of *Salmonella* species in poultry environmental samples," Journal Microbiology Methods, 2004, pp. 285-288, vol. 58.
Notermans, S., et al.; "Immunological methods for detection of foodborne pathogens and their toxins," International Journal of Food Microbiology, 1991, pp. 91-102, vol. 12.
Favrin, Stacy J., et al., "Application of a novel immunomagnetic separation-bacteriophage assay for the detection of *Salmonella ententidis* and *Escherichia coli* O157:H7 in food," International Journal of Food Microbiology, 2003, pp. 63-71, vol. 85.
Feng, Peter, et al.; "Genetic Analysis for Virulence Factors in *Escherichia coli* O104:H21 That was Implicated in an Outbreak of Hemorrhagic Colitis," Journal of Clinical Microbiology, 2001, pp. 24-28.
Heo, Jinseok, et al.; "An Overview of Recent Strategies in Pathogen Sensing," Sensors, 2009, pp. 4483-4502, vol. 9.
Lin, Frank Y. H., et al.; "Development of a Nanoparticle-Labeled Microfluidic Immunoassay for Detection of Pathogenic Microorganisms," Clinical and Diagnostic Laboratory Immunology, 2005, pp. 418-425, vol. 12.
Jay, James M.; "Modern food microbiology," Book, 3rd Edition, 1986.
Tenover, Fred C., :DNA Probes for Infectious Diseases, Book, CRC Press, 1989.

*Primary Examiner* — Albert Navarro
(74) *Attorney, Agent, or Firm* — Tristan A. Fuierer; Andrew D. Gerschutz; Moore & Van Allen, PLLC

(57) ABSTRACT

The present invention relates to a method of rapidly detecting microorganisms using nanoparticles, and more particularly to a method and device of rapidly detecting microorganisms by adding, to the microorganisms to be detected, nanoparticles having immobilized thereon an antibody that binds specifically to the microorganisms to be detected, subjecting the mixture to an immune reaction to form a reaction solution, passing the reaction solution through a microorganism-concentrating film to concentrate the microorganisms, capturing microorganisms, which was immune-reacted with the antibody-immobilized nanoparticles, by a microorganism-capturing filtration membrane, and determining the presence and concentration of the microorganisms.

The present invention detects microorganisms using nanoparticles having immobilized thereon an antibody that binds specifically to the microorganisms to be detected, so that the presence and concentration of the microorganisms can be determined in a more effective and simpler manner than a conventional detection method, and the inventive method is effective in detecting a small amount of microorganisms owing to high sensitivity.

15 Claims, 4 Drawing Sheets

METHOD OF RAPIDLY DETECTING MICROORGANISMS USING NANOPARTICLES

CROSS-REFERENCE TO RELATED APPLICATIONS

This application is filed under the provisions of 35 U.S.C. §371 and claims the priority of International Patent Application No. PCT/KR2010/008356 filed on 24 Nov. 2010 entitled "METHOD OF RAPIDLY DETECTING MICROORGANISMS USING NANOPARTICLES" in the name of Min Gon KIM, et al., which claims priority to Korean Patent Application No. 10-2009-0114138 filed on 24 Nov. 2009, both of which are hereby incorporated by reference herein in their entirety.

TECHNICAL FIELD

The present invention relates to a method of rapidly detecting microorganisms using nanoparticles, and more particularly to a method and a device of rapidly detecting microorganisms by adding, to a microorganisms to be detected, nanoparticles having immobilized thereon an antibody that binds specifically to the microorganisms to be detected, subjecting the mixture to an immune reaction, passing the reaction solution through a microorganism-concentrating film to concentrate the microorganisms, capturing microorganisms, which was immune-reacted with the antibody-immobilized nanoparticles, by a microorganism-capturing filtration membrane, and determining the presence and concentration of the microorganisms.

BACKGROUND ART

Rapid microbial detection is very important for the detection of foodborne pathogenic microorganisms, the detection of environmentally harmful bacteria, the detection of infectious bacteria, the diagnosis of pathogenic virus, and the like. Methods for determining the presence and concentration of pathogenic substances (microorganisms, proteins, etc.), which are generally frequently used, include a colony assay, a DNA probe assay, an immunoassay, and the like (Jay J M. Modern Food Microbiology, 1986, 3rd, ed., p 95, Van Nostrand Reinhold Co., New York; Tenover F C., DNA Probes for Infectious Diseases, 1989, p 53 CRC Press, Boca Raton).

In the colony assay, a sample is collected and incubated in a selective medium composed of components selected such that only the type of microorganisms to be detected can survive, after which the number of colonies by the microorganisms is measured. This assay method is very accurate, but has disadvantages in that a long time is required for measurement and it is difficult to select a medium for each type of microorganisms.

The DNA probe assay includes real-time PCR (polymerase chain reaction) and nucleic acid hybridization. In this method, microorganisms are physically and chemically destroyed, and then DNA in the microbial cells is detected by nucleic acid hybridization. Although this method has an advantage in that the test time is shorter than that in the colony assay method, it has disadvantages in that an expensive PCR system is used and when a small amount of microorganisms are to be detected, a separate culture step should be carried out in order to attain high sensitivity (Ninet, B et al., *Appl Environ Microbiol,* 58:4055-4059, 1992). If the culture step is not carried out, dead cells can be detected, resulting in incorrect results. In addition, when PCR is carried out, false-positive reactions can very frequently occur to increase the detection error and reduce the reliability of analysis.

The immunoassay method is based on an antigen-antibody binding reaction. For example, an enzyme-linked immunosorbent assay (ELISA) which uses an antibody specific to a surface antigen of the microorganisms to be detected is widely known. This method shows high sensitivity in a short time, and thus is considered as a substitute for the above-described two methods. In this method, an antibody can be continuously produced by a hybridoma, and thus the occurrence of problems can be minimized. However, such a immunoassay method has a drawback in that a highly pure antigen, an expensive system, and a long-term test are required.

Another antibody-based assay is an immunomagnetic separation (IMS) method, which can shorten enrichment time and can selectively capture bacteria by employing specific antibodies bound to magnetic particles or beads (Lynch, M J et al., *J Microbiol Methods* 58:285-288, 2004; Notermans, S et al., *Int J Food Microbiol,* 12:91-102, 1991). IMS is used to capture and concentrate selective target organisms, proteins, or nucleic acids (Favrin, S J et al., *Int J Food Microbiol,* 85:63-71, 2003; Feng P., *ASM press, Washington D.C.,* 2001). Like other antibody-based assays, however, IMS also requires an enrichment process and is limited for use on small volume samples.

SPR sensor technology is a method of detecting microorganisms using a phenomenon in which a signal change occurs when biomaterials such as proteins are bound to the sensor surface. This method requires a short detection time and a simple assay procedure, compared to other assay methods. However, because the size of pathogenic microorganisms in a sample is much larger than an antibody immobilized on the sensor surface, the efficiency of binding of the microorganisms to the antibody by an immune response in a fluid flow in the SPR system is low. As a result, due to the inefficient immune reaction of the antibody and the immobilization of the antibody on the sensor surface, the detection limit of pathogenic microorganisms is disadvantageously high.

Accordingly, the present inventors have made extensive efforts to solve the above-described problems and, as a result, have found that the high-sensitivity detection and analysis of microorganisms can be achieved using not only an immune reaction with nanoparticles, which have immobilized thereon an antibody that binds specifically to the microorganisms to be detected, but also a membrane filtration method, thereby completing the present invention.

DISCLOSURE OF INVENTION

It is a main object of the present invention to provide a method of rapidly detecting microorganisms using not only nanoparticles, which have immobilized thereon an antibody that binds specifically to the microorganisms to be detected, but also a membrane filtration method.

Another object of the present invention is to provide a device for rapidly detecting microorganisms, which comprises nanoparticles having immobilized thereon an antibody that binds specifically to the microorganisms to be detected.

To achieve the above objects, the present invention provides a method of rapidly detecting microorganisms using nanoparticles, the method comprising the steps of: (a) mixing and reacting nanoparticle-antibody conjugates, which bind specifically to the microorganisms to be detected, with a sample containing the microorganisms to be detected, thereby obtaining a reaction solution; (b) passing the reaction solution through a microorganism-concentrating film and then through a microorganism-capturing filtration membrane so as to permeate nanoparticle-antibody conjugates, which did not react with the microorganisms, and to selectively capture a nanoparticle-antibody-microorganism composite; and (c) determining the presence or concentration of the nanoparticle-antibody-microorganism composite captured by the filtration membrane.

The present invention also provides a device for detecting microorganisms, comprising: a sample reaction unit comprising nanoparticles having immobilized thereon an antibody that binds specifically to the microorganisms to be detected; a microorganism-concentrating film which receives a reaction solution from the sample reaction unit and concentrates the microorganisms to be detected; a microorganism-capturing filtration membrane which captures and selectively separates the concentrated microorganisms that passed through the microorganism-concentrating film; and a detection unit for determining the presence or concentration of the microorganisms.

BEST MODE FOR CARRYING OUT THE INVENTION

Figure 1:
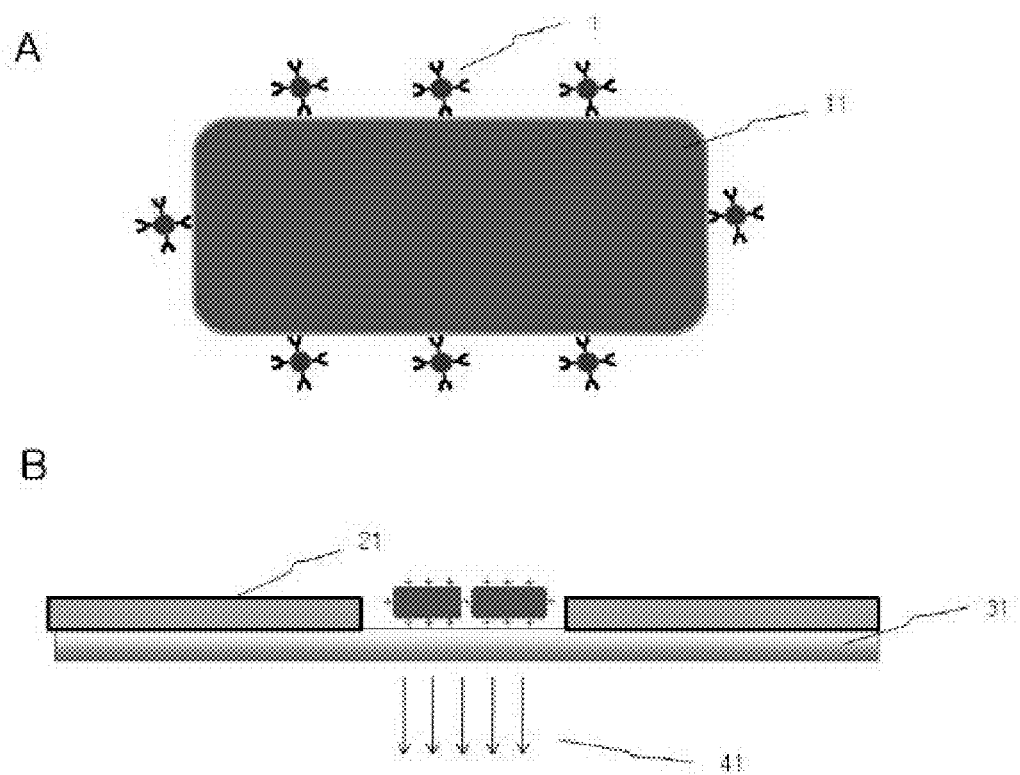
FIG. 1 is a schematic diagram showing that the concentration of microorganisms can be determined by the selective binding of AuNP-antibody conjugates to microorganisms.

Unless defined otherwise, all technical and scientific terms used herein have the same meaning as commonly understood by one of ordinary skill in the art to which the invention pertains. Generally, the nomenclature used herein and the experiment methods which will be described later are well known and commonly employed in the art.

Hereinafter, the present invention will be described in detail.

In one aspect, the present invention is directed to a method of rapidly detecting microorganisms using nanoparticles, the method comprising the steps of: (a) mixing and reacting nanoparticle-antibody conjugates, which bind specifically to the microorganisms to be detected, with a sample containing the microorganisms to be detected, thereby obtaining a reaction solution; (b) passing the reaction solution through a microorganism-concentrating film and then through a microorganism-capturing filtration membrane so as to permeate nanoparticle-antibody conjugates, which did not react with the microorganisms, and to selectively capture a nanoparticle-antibody-microorganism composite; and (c) determining the presence or concentration of the nanoparticle-antibody-microorganism composite captured by the filtration membrane.

In the present invention, the microorganisms to be detected may be foodborne pathogenic microorganisms, viruses, infectious microorganisms, or the like, and examples thereof include *E. coli, Listeria monocytogenes, Salmonella typhimurim, Staphylococcus aureus*, norovirus, and the like.

In the present invention, the antibody that binds specifically to the microorganisms to be detected is not specifically limited and may be any antibody known to bind specifically to microorganisms known in the art. For example, to detect *Staphylococcus* species, ab20002 (Abcam) known as an antibody that binds specifically to the *Staphylococcus* species may be used.

In the present invention, the nanoparticles may be metal nanoparticles, quantum dot nanoparticles, or magnetic nanoparticles (MNPs), in which the metal may be selected from the group consisting of gold (Au), silver (Ag), and copper (Cu).

As used herein, the term "nanoparticles" refers to ultrafine particles having a size of about 1-200 nm. Nanoparticles having a very small size have properties different from those of general mass materials. Nanoparticles have a specific surface area significantly higher than other materials. Due to their high specific surface area, nanoparticles have surface effects different from other materials, and as the size of nanoparticles decreases, the number of molecules located on the surface of the nanoparticles increases. When the diameter of particles becomes 5 nm, 50% of molecules constituting the particles are located on the particle surface, and when the size of particles becomes 2 nm, the ratio of molecules located on the particle surface reaches 90%.

Nanoparticles have a surface energy-to-binding energy ratio higher than other materials, because the ratio of molecules located on the surface is relatively high. The ratio of surface energy to binding energy increases from 5% to 30% as the particle size decreases from 20 nm to 1 nm. Atoms constituting particles are in a stable energy state in the attractive and repulsive forces are balanced by the interaction between the surrounding atoms. However, atoms located on the particle surface are in a high energy state, because only an attractive force caused by the internal atoms exists. Due to such surface effects, nanoparticles have properties such as surface activity, which appears in catalysts or catalytic surface reactions, low melting points, and low-temperature sintering properties.

In one example of the present invention, gold nanoparticles having a size of about 20 nm were used, but are not limited thereto. It will be obvious to those skilled in the art that gold nanoparticles may have any particle diameter which does not interfere with an immune reaction between an antibody and an analysis material. Preferably, the nanoparticles have a diameter of 5-100 nm.

In one embodiment of the present invention, the nanoparticles may be magnetic nanoparticles. Because of the properties of the magnetic nanoparticles, the method of rapidly detecting microorganisms according to the present invention may further comprise, after the step of mixing and reacting the sample with the conjugates, a step of separating the magnetic nanoparticle-antibody-microorganism composite from the reaction solution by a magnet and suspending the separated composite in a buffer solution, whereby more complete detection of microorganisms can be achieved.

In one example of the present invention, detection of microorganisms using magnetic nanoparticles was performed by mixing and reacting magnetic nanoparticle-antibody conjugates with a sample containing the microorganisms to be detected, thereby obtaining a reacting solution, separating the resulting magnetic nanoparticle-antibody-microorganism composite from the reaction solution using a magnet at room temperature, removing the supernatant from the reaction solution, suspending the separated composite in a buffer solution, passing the suspension through a microorganism-concentrating film and then a microorganism-capturing filtration membrane, and identifying the nanoparticle-antibody-microorganism composite included in the filtration membrane. In addition, it was found that the microorganisms could be detected at various concentrations. This suggests that a separation and detection method of obtaining the material of interest from a suspension containing various impurities can be more effectively performed using a magnetic force.

In another embodiment of the present invention, the nanoparticles may be quantum dot nanoparticles, whereby two or more species of microorganisms can be simultaneously detected.

Herein, the quantum dot nanoparticles are semiconductor nanoparticles having unique optical characteristics. If the particle size of the quantum dot nanoparticles is changed a little or if the composition thereof is changed even a little, the nanoparticles will emit a strong fluorescent light having a different wavelength. After the quantum dot nanoparticles have absorbed light, they emit a fluorescent light having a wavelength different from that of the absorbed light. This phenomenon can be easily controlled, and thus the quantum dot nanoparticles can be used in various applications. Accordingly, when the nanonarticles having immobilized thereon an antibody that binds specifically to the microorganisms to be detected, which are used in the present invention, are quantum dot nanoparticles, two or more species of microorganisms can be simultaneously detected. The quantum dot nanoparticles can be prepared according to any method known in the art.

In the present invention, the microorganism-concentrating film may have a plurality of holes having a diameter of 0.1-5 mm.

The microorganism-concentrating film is a device through which microorganisms pass before passage through the filtration membrane. It allows microorganisms to be concentrated at one place, thereby obtaining a larger signal. As the size of the holes of the microorganism-concentrating film decreases, microorganisms can be more densely concentrated, and thus a larger signal can be obtained. The detection limit of microorganisms in a conventional immunofiltration method is $10^5$ cfu, but in one example of the present invention, it was found that the use of the microorganism-concentrating film enabled microorganisms to be detected at a density of $10^2$ cfu.

In the present invention, the microorganism-concentrating film may be made of a material selected from the group consisting of PDMS (polydimethylsiloxane), a viscous polymer, an aluminum tape, rubber, latex, and a paste for screen printing.

In the most preferred embodiment of the present invention, the microorganism-concentrating film may be a film prepared by applying a screen-printing paste such as a silver or carbon paste to the microorganism-capturing filtration membrane by a screen printing technique so as to have holes of a predetermined size. Thus, the microorganism-concentrating film and the microorganism-capturing film can be formed integrally with each other. In addition, the screen printing technique that is used in the present invention may be any method widely known in the art.

For example, the screen printing technique can be performed by fixing a screen mesh made of nylon, polyester or stainless steel to a frame made of wood or aluminum, forming a sheet thereon by a manual or photochemical method to close up portions other than a necessary image, applying a screen-printing paste thereto, and pressing and moving the inner surface of the screen mesh with a squeegee to allow the paste to pass through the mesh portions on which the sheet was not formed, thereby printing the paste on a substrate located below the sheet.

In the present invention, the microorganism-capturing filtration membrane preferably has a pore size ranging from 100 nm to 10 μm.

The antibody-immobilized nanoparticles unbound to microorganisms will pass through the microorganism-capturing filtration membrane, and microorganisms unbound to the antibody-immobilized nanoparticles will show no signal even when they are captured by the filtration membrane. Thus, only microorganisms bound to the antibody-immobilized nanoparticles will show the characteristic color and fluorescence of the antibody-immobilized nanoparticles in the microorganism-capturing filtration membrane.

In one example of the present invention, a microorganism-capturing filtration membrane having a pore size of about 1.2 μm was used, but the scope of the present invention is not limited thereto. Preferably, the microorganism-capturing filtration membrane may have a pore size between 100 nm and 10 μm at which microorganisms that reacted with the antibody-immobilized nanoparticles are captured.

In the present invention, the microorganism-capturing filtration membrane may be made of a material selected from the group consisting of nitrocellulose, polycarbonate, nylon, polyester, cellulose acetate, polysulfone, and polyethersulfone.

In the method of rapidly detecting microorganisms according to the present invention, the step (b) may be performed by using vacuum, centrifugation, or absorption.

In other words, when the nanoparticle-antibody-microorganism composite is filtered by the microorganism-capturing filtration membrane after passage through the microorganism-concentrating film, it can be selectively separated by application of vacuum, centrifugation, or absorption into the filtration membrane. In the examples described below, the nanoparticle-antibody-microorganism composite was adsorbed onto the filtration membrane by applying a vacuum. In addition to this adsorption method, various adsorption methods known in the art may be used in the present invention. When the nanoparticles are magnetic nanoparticles, the composite can be selectively attracted using a magnet, whereby microorganisms other than the microorganisms to be detected can be excluded from analysis.

In the method of rapidly detecting microorganisms according to the present invention, determining of the step (c) may be measured using a CCD camera or absorbance.

In the examples described below, nanoparticle-antibody-microorganism composite spots were observed by a CCD camera. In addition, nanoparticles such as gold or silver nanoparticles show their characteristic absorbance in the UV-V is region by the surface plasmon phenomenon. Thus, the nanoparticles that are used in the present invention absorb light at a specific wavelength and enable the concentration of microorganisms to be determined by measuring the absorbance at a wavelength corresponding to the property of the nanoparticles.

In another aspect, the present invention is directed to a device for detecting microorganisms, comprising: a sample reaction unit comprising nanoparticles having immobilized thereon an antibody that binds specifically to the microorganisms to be detected; a microorganism-concentrating film which receives a reaction solution from the sample reaction unit and concentrates the microorganisms to be detected; a microorganism-capturing filtration membrane which captures and selectively separates the concentrated microorganisms that passed through the microorganism-concentrating film; and a detection unit for determining the presence or concentration of the microorganisms.

As used herein, the expression "sample reaction unit" refers to a portion comprising nanoparticles having immobilized thereon an antibody that binds specifically to the microorganisms to be detected, in which the nanoparticles react with a sample containing the microorganisms to be detected. The sample reaction unit that is used in the present invention may be any device capable of mixing the nanoparticles with the sample and may, for example, be a test tube.

In the present invention, the detection unit may be any device capable of determining the presence or concentration of the nanoparticle-antibody-microorganism composite. Preferably, it is a CCD image detector, a CMOS image detector, a CCD fluorescence detector, a PMT fluorescence detector, or the like. For example, it may be a CCD camera or an absorbance-measuring device. In the present invention, the features of the nanoparticles, the microorganism-concentrating film, and the microorganism-capturing filtration membrane are as described above.

In the present invention, the microorganisms to be detected may be foodborne pathogenic microorganisms, viruses, infectious microorganisms, or the like, and examples thereof include *E. coli, Listeria monocytogenes, Salmonella typhimurim, Staphylococcus aureus*, norovirus, and the like.

In the device of detecting microorganisms according to the present invention, the sample reaction unit, the microorganism-concentrating film, the microorganism-capturing filtration membrane and the detection unit may be provided separately from each other or integrally with each other. Preferably, the microorganism-concentrating film may be a film prepared by applying a screen-printing paste such as a silver or carbon paste to the microorganism-capturing filtration membrane by a screen printing technique so as to have holes of a predetermined size. Thus, the microorganism-concentrating film and the microorganism-capturing film can be formed integrally with each other.

EXAMPLES

Hereinafter, the present invention will be described in further detail with reference to examples. It will be obvious to a person having ordinary skill in the art that these examples are illustrative purposes only and are not to be construed to limit the scope of the present invention. That is, the following steps will be described as one illustrative ones and do not limit the scope of the present invention.

Example 1

Fabrication of PDMS (Polydimethylsiloxane) Film for Microbial Concentration

A microorganism-concentrating film was prepared in the following manner.

A PDMS solution (Sylgard 184A, Dow Corning, USA) and a curing agent (Sylgard 184B, Dow Corning, USA) were mixed at a ratio of 10:1, and the mixture was poured into a flat Petri dish having a diameter of 150 mm. Then, the mixture was defoamed using a vacuum pump and cured at 60 r for 24 hours. The cured PDMS film was cooled at room temperature, and then 7 holes having a diameter of 1.5 mm were formed through the film using a perforator.

As a result, it was confirmed that a PDMS film having holes was prepared.

Example 2

Culture of Microorganisms

*Listeria monocytogenes* and *Salmonella typhimurium* stocks were obtained, inoculated into a BHI (brain heart infusion) broth and cultured in a shaking incubator at 37° C. for 18-24 hours. Meanwhile, *Escherichia coli* was inoculated into LB (Luria Bertani) broth, and *Staphylococcus aureus* was inoculated into NB (nutrient broth), and these microorganisms were cultured under the same conditions as above. To measure the colony forming unit (cfu) of the cultured microorganisms, each species of the cultured microorganisms was serially diluted to a dilution factor of $10^5$-$10^9$, and 100 µl of each of the dilutions was plated on a solid medium and then cultured at 37° C. for 16-24 hours. Then, the number of viable microbial cells was determined by counting the number of colonies formed and multiplying the colony count by the dilution factor. In addition, a suitable amount of the liquid medium of the microorganisms being cultured was measured for absorbance at 600 nm.

Example 3

Rapid Detection of Microorganisms Using Gold Nanoparticles (Hereinafter, Referred to as AuNP)-Antibody Conjugates 3-1: Preparation of AuNP-Antibody Conjugates To 1 ml of 20-nm AuNP solution (BB International), 0.1 ml of borate buffer (0.1M, pH 8.5), and 10 µg of an antibody (Abcam, ab20002) specific to *Staphylococcus aureus* were added. After 30 minutes, 0.1 ml of 1% BSA (bovine serum albumin) solution (pH 8.5; in 10 mM carbonate buffer) was added thereto, and the resulting solution was allowed to stand for 30 minutes. Then, the solution was centrifuged at 4° C. at 10,000 rpm for 20 minutes, and the supernatant was removed. 1 ml of 0.1% BSA (pH 8.5; in 10 mM carbonate buffer) was added to mixed with the residue, which was then centrifuged at 10,000 rpm for 20 minutes, and the supernatant was removed. The above centrifugation process was repeated once more, after which 0.5 ml of 0.1% BSA (in PBS buffer) was added thereto, and the resulting solution was stored in a refrigerator.

As a result, an AuNP-antibody conjugate solution was successfully prepared. FIG. 1 is a schematic diagram showing that the concentration of microorganisms can be determined by the selective binding of such AuNP-antibody conjugates. When the AuNP-antibody conjugates are mixed and reacted with a sample, a mixture as shown in FIG. 1A will be formed. When the mixture of FIG. 1A is introduced into the device shown in FIG. 1B, the microorganisms will be captured, and unreacted AuNP-antibody conjugates will pass through the device, and only the microorganisms to which the composites have been selectively bound can show the color of AuNP.

In FIG. 1, the reference numerals of main elements are as follows:
1: AuNP-antibody conjugates
11: microorganisms
21: microorganism-concentrating film
31: microorganism-capturing filtration membrane
41: absorption flow of an aqueous solution by a vacuum or an adsorbing membrane.

3-2: Rapid Detection of *Staphylococcus aureus* Microorganisms

The *Staphylococcus aureus* microorganisms cultured according to the method described in Example 2 was suspended in PBS, and 100 μl (0-$10^5$ cfu) of the suspension was mixed with 50 μl of the AuNP-antibody conjugate solution prepared according to the method of Example 3-1. The mixture was mildly shaken for 30 minutes.

The microorganism-capturing filtration membrane used in this Example was prepared by applying 1% BSA solution (in distilled water) to a nitrocelluolose (NC) membrane (Millipore) having a pore size of 1.2 μm and then drying the applied solution. The NC membrane was placed on a filter provided in a 100 mL erlenmeyer flask having a branch, and then the PDMS film prepared in Example 1 was applied to the NC membrane. A vacuum was applied to the flask through the branch, while the mixture of the AuNP-antibody conjugates and *Staphylococcus aureus* was passed through the holes of the PDMS film, and the concentration of *Staphylococcus aureus* was determined.

Figure 2:
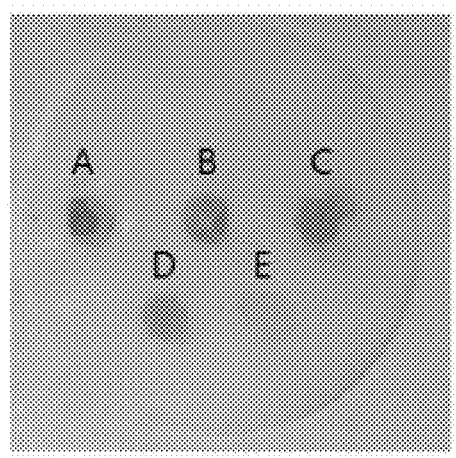
FIG. 2 shows the results obtained by measuring various concentrations of *Staphylococcus aureus* using AuNP-antibody conjugates comprising an antibody specific to *Staphylococcus aureus* (A: $10^5$ cfu; B: $10^4$ cfu; C: $10^3$ cfu; D: $10^2$ cfu; E: absence of cells).

As a result, as shown in FIG. 2, in the case in which *Staphylococcus aureus* was absent, the AuNP-antibody conjugates did not remain on the filtration membrane. In addition, as the concentration of *Staphylococcus aureus* increased, the amount of AuNP remaining on the filtration membrane increased. In FIG. 2, A: $10^5$ cfu; B: $10^4$ cfu; C: $10^3$ cfu; D: $10^2$ cfu; and E: absence of cells. Thus, it can be seen that the microorganisms can be measured at various concentrations and can be measured up to at least $10^2$ cfu. This concentration corresponds to sensitivity 1000 times higher than $10^5$ cfu which could be measured by a conventional immunofiltration method, suggesting that the method of the present invention has sensitivity significantly higher than the immunofiltration method.

3-3: Examination of Cross-Reaction with Other Microbial Species

In order to confirm whether the microbial detection method of the present invention can selectively detect microorganisms using the nanoparticle-antibody conjugates, a test was performed for various species of microorganisms using the AuNP-antibody conjugates in the same manner as Example 3-2.

Specifically, the AuNP-anti-*Staphylococcus aureus* conjugates were allowed to react with a total of 4 species of microorganisms (*Staphylococcus aureus, Listeria monocytogenes, Salmonella typimurium*, and *Escherichia coli*), and then the reaction products were analyzed.

Figure 3:
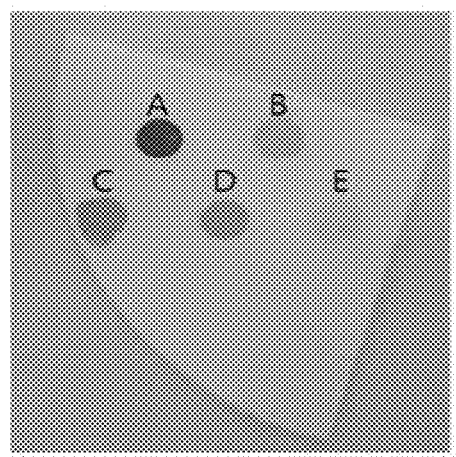
FIG. 3 shows the results of a test performed to determine whether AuNP-antibody conjugates comprising an antibody specific to *Staphylococcus aureus* cross-react with other species of microorganisms (A: $10^6$ cfu *S. aureus* cells; B: $10^6$ cfu *E. coli* cells; C: $10^6$ cfu *Salmonella* cells; D: $10^6$ cfu *Listeria monocytogenes* cells; E: absence of cells).

As a result, as can be seen in FIG. 3, AuNP did not appear in *Listeria monocytogenes, Salmonella typimurium* and *Escherichia coli*, but appeared specifically in *Staphylococcus aureus*. In FIG. 3, A: $10^6$ cfu *S. aureus* cells; B: $10^6$ cfu *E. coli* cells; C: $10^6$ cfu *Salmonella* cells; D: $10^6$ cfu *Listeria monocytogenes* cells; E: absence of cells. This demonstrates that the detection method according to the present invention can be used specifically to detect the microorganisms of interest.

3-4: Detection of *Listeria monocytogenes* Microorganisms and Examination of Cross-Reaction with Other Microbial Species In order to confirm whether the microbial detection method of the present invention can selectively detect microorganisms using AuNP-antibody conjugates, a test was performed for various species of microorganisms according to the methods of Examples 3-2 and 3-3 using AuNP-antibody conjugates comprising an antibody (Abcam, ab30747) specific to *Listeria monocytogenes*.

Specifically, the AuNP-anti-*Listeria monocytogenes* conjugates were allowed to react with *Staphylococcus aureus, Listeria monocytogenes, Salmonella typimurium* and *Escherichia coli*, and then the reaction products were analyzed. For comparison, AuNP-BSA conjugates in place of the AuNP-antibody conjugates were synthesized and allowed to react with microbial species, and the reaction products were analyzed.

Figure 4:
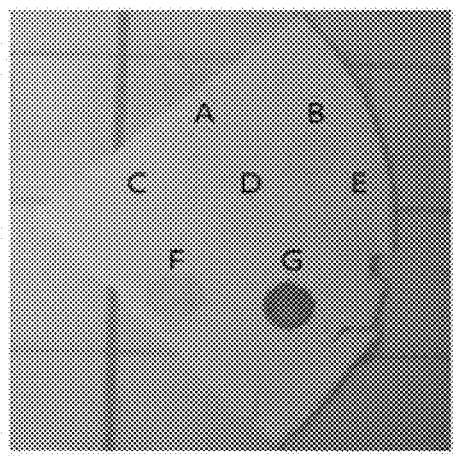
FIG. 4 shows the results of a test performed to determine whether AuNP-antibody conjugates comprising an antibody specific to *Listeria monocytogenes* cross-react with other species of microorganisms (A-C: reacted with AuNP-BSA conjugates; A: $10^5$ cfu *Listeria monocytogenes* cells; B: AuNP-anti-*Listeria monocytogenes*; C: $10^5$ cfu *Listeria monocytogenes* cells; D-G: reacted with AuNP-antibody conjugates; D: $10^5$ cfu *Salmonella typimurium* cells; E: $10^5$ cfu *Escherichia coli* cells; F: $10^5$ cfu *Staphylococcus* cells; G: $10^5$ cfu *Listeria monocytogenes* cells).

As a result, as can be seen in FIG. 4, only *Listeria monocytogenes* could be selectively detected. In FIG. 4, A-C: reacted with AuNP-BSA conjugates; A: $10^5$ cfu *Listeria monocytogenes* cells; B: AuNP-anti-*Listeria monocytogenes*; C: $10^5$ cfu *Listeria monocytogenes* cells; D-G: reacted with AuNP-antibody conjugates; D: $10^5$ cfu *Salmonella* typimurium cells; E: $10^5$ cfu *Escherichia coli* cells; F: $10^5$ cfu *Staphylococcus* cells; G: $10^5$ cfu *Listeria monocytogenes* cells.

Example 4

Rapid Detection of Microorganisms Using Magnetic Nanoparticle (Hereinafter, Referred to as MNP)-Antibody Conjugates 4-1: Preparation of Magnetic Nanoparticle (MNP)-Antibody Conjugates To 100 μl of 100-nm MNP solution (Chemicell), EDC (1-ethyl-3-(3-dimethylaminopropyl)carbodiimide) and an antibody were added to final concentrations of 66.7 mg/mL and 100 μg/mL, respectively. After 2 hours, magnetic nanoparticles were separated from the solution by a magnet for 2 minutes, and then the supernatant was removed. Then, 200 μl of PBS solution was added to and mixed with the magnetic nanoparticles, after which MNPs were separated from the solution by a magnet for 2 minutes, and the supernatant was removed. After the above separation procedure was repeated once more, 0.4 ml of 0.1% BSA solution (in PBS buffer) was added to and mixed with MNPs, which were then filtered through a 0.2 μm syringe filter. The filtered solution was stored in a refrigerator.

Figure 5:
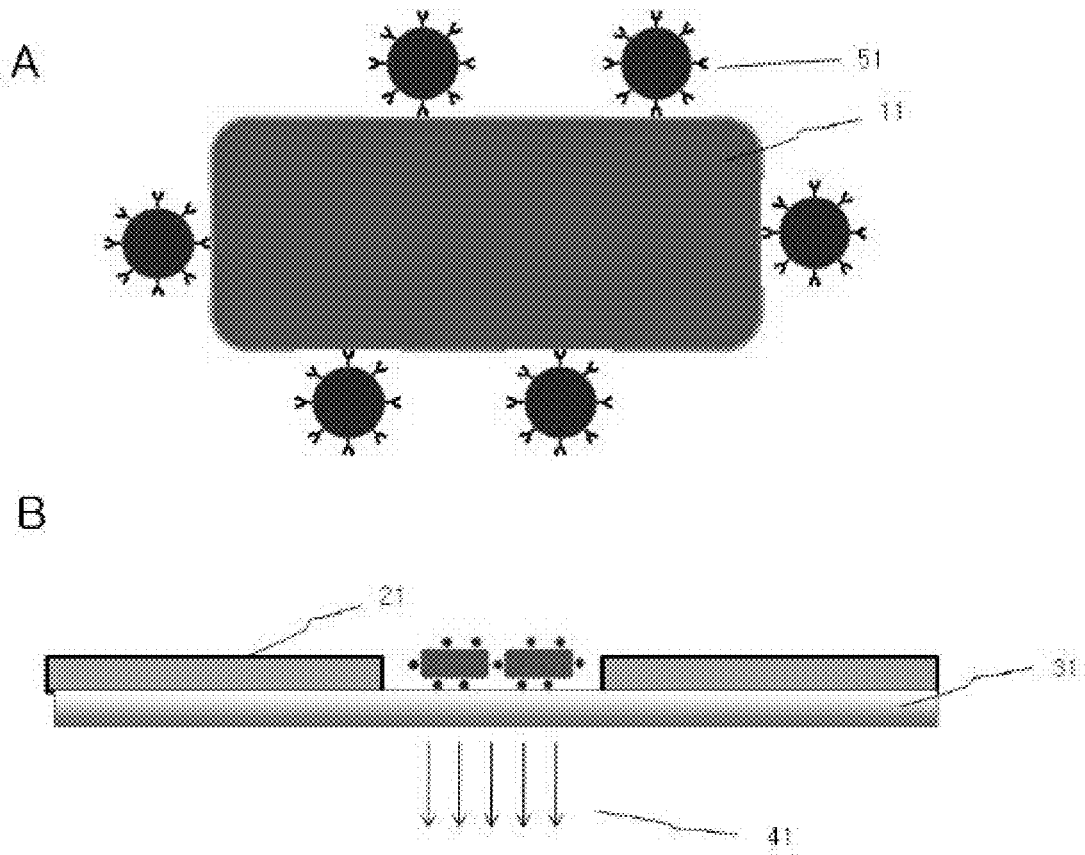
FIG. 5 is a schematic diagram showing that the concentration of microorganisms can be determined by the selective binding of MNP-antibody conjugates to microorganisms.

As a result, an MNP-antibody conjugate solution was successfully prepared. FIG. 5 shows a schematic diagram showing that the concentration of microorganisms can be determined by the selective binding of such MNP-antibody conjugates and the microorganisms. When the MNP-antibody conjugates are mixed and reacted with a sample, a mixture as shown in FIG. 5A will be formed. When the mixture is collected by a magnet and a suspension of the collected mixture in an aqueous solution is introduced into the device shown in FIG. 5B, microorganisms will be captured, and unreacted MNP-antibody conjugates will pass through the device, and the microorganisms to which the composites have been selectively bound as shown in FIG. 5A can show the color of MNP.

The reference numerals of main elements are as follows:
51: MNP-antibody conjugates
11: microorganisms
21: Concentrating film
31: microorganism-capturing filtration membrane
41: absorption flow of an aqueous solution by a vacuum or an adsorbing membrane.

4-2: Rapid detection of *Staphylococcus aureus* microorganisms

*Staphylococcus aureus* cultured according to the method described in Example 2 was suspended in 0.1% BSA (in PBS-0.05% Tween 20 buffer), and 10 μl (0, $10^5$ or $10^6$ cfu) of the suspension was mixed with 30 μl of the MNP-anti-*Staphylococcus aureus* (Abcam) conjugate solution prepared according to the method of Example 4-1 and 160 μl of 0.1% BSA solution (in PBS-0.05% Tween 20 buffer). The mixture was mildly shaken for 30 minutes. After 30 minutes, the magnetic nanoparticle-antibody conjugates that reacted with *Staphylococcus aureus* were separated from the solution by a magnet for 5 minutes, and then the supernatant was removed. 200 μl of 0.1% BSA solution (PBS-0.05% Tween 20 buffer) was added to and mixed with the reaction product.

The microorganism-capturing filtration membrane used in this Example was prepared by applying 1% BSA solution (in distilled water) to a nitrocelluolose (NC) membrane (Millipore) having a pore size of 1.2 μm and then drying the applied solution. The NC membrane was placed on a filter provided in a 100 mL erlenmeyer flask having a branch, and then the PDMS film prepared in Example 1 was applied to the NC membrane. A vacuum was applied to the flask through the branch, while the mixture of the MNP-antibody conjugates and *Staphylococcus aureus* was passed through the holes of the PDMS film, and the concentration of *Staphylococcus aureus* was determined.

Figure 6:
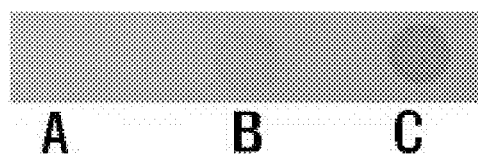
FIG. 6 shows the results obtained by measuring various concentrations of *Staphylococcus aureus* using MNP-antibody conjugates comprising an antibody specific to *Staphylococcus aureus* (A: absence of microorganisms; B: $10^5$ cfu; C: $10^6$ cfu).

As a result, as shown in FIG. 6, the amount of MNP remaining on the membrane increased as the concentration of *Staphylococcus aureus* increased. Thus, it could be seen that microorganisms can be detected at various concentrations, suggesting that the material of interest can be separated from a suspension containing various impurities using a magnetic force. In FIG. 6, A: absence of microorganisms; B: $10^5$ cfu; and C: $10^6$ cfu.

Example 5

Preparation of Microorganism-Concentrating Film Using Screen-Printing Paste

In order to prepare a film having three holes of various sizes (0.15, 0.3, 0.5 and 0.75 mm), a mesh was prepared, and a polysulfone membrane (Pall Life Sciences; pore size: 0.45 μm) was placed thereon, and then a silver past was screen-printed on a surface of the membrane, which had a relatively smaller pore size.

Figure 7:
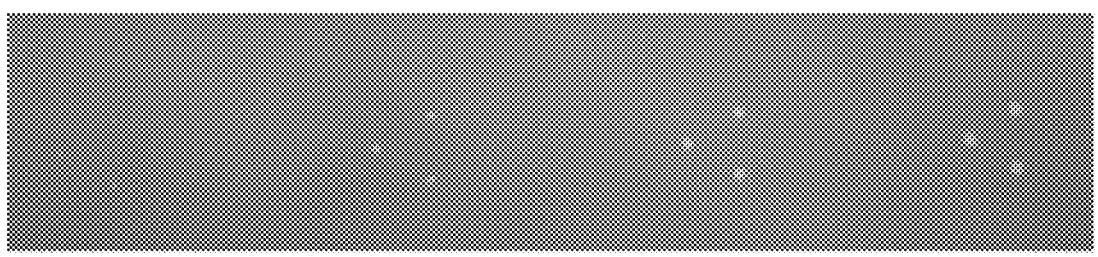
FIG. 7 is a photograph showing a microorganism-concentrating film/microorganism-capturing filtration membrane prepared using a paste for silver (Ag) screen printing.

As a result, as shown in FIG. 7, a microorganism-concentrating film integrated with a membrane-capturing filtration membrane could be obtained. In addition, when the technology of this Example was used, a microorganism-concentrating film with small holes having a size of about 0.1 mm could be obtained.

As described above in detail, the inventive method and system of rapidly detecting microorganisms using nanoparticles can be usefully utilized to detect microorganisms in a cost-effective and simple manner.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

INDUSTRIAL APPLICABILITY

The present invention rapidly detects microorganisms using nanoparticles having immobilized thereon an antibody that binds specifically to the microorganisms to be detected. The nanoparticles can be detected directly without a secondary reaction with a probe, which is complex and time-consuming, whereby the presence and concentration of the microorganisms are determined in an effective and simple manner. In addition, a conventional immunofiltration method can detect microorganisms up to a concentration of $10^5$ cfu, but the microorganism detection method of the invention can detect microorganisms up to a concentration of $10^2$ cfu, and thus is effective in detecting a small amount of microorganisms.

What is claimed is:

1. A method of rapidly detecting microorganisms using nanoparticles, the method comprising the steps of:

(a) mixing and reacting nanoparticle-antibody conjugates, which bind specifically to the microorganisms to be detected, with a sample containing the microorganisms to be detected, thereby obtaining a reaction solution;

(b) passing the reaction solution through a microorganism-concentrating film and then through a microorganism-capturing filtration membrane so as to permeate nanoparticle-antibody conjugates, which did not react with the microorganisms, and to selectively capture a nanoparticle-antibody-microorganism composite; and (c) determining the presence or concentration of the nanoparticle-antibody-microorganism composite captured by the filtration membrane.

2. The method of claim 1, wherein the nanoparticles are metal nanoparticles, quantum dot nanoparticles, or magnetic nanoparticles (MNPs).

3. The method of claim 2, wherein the metal is selected from the group consisting of gold (Au), silver (Ag), and copper (Cu).

4. The method of claim 1, wherein the nanoparticles are magnetic nanoparticles (MNPs), and the step (a) further comprises a step of separating the magnetic nanoparticle-antibody-microorganism composite from the reaction solution by a magnet and suspending the separated composite in a buffer solution, after the step of mixing and reacting with the sample.

5. The method of claim 1, wherein the nanoparticles are quantum dot nanoparticles, and two or more species of microorganisms are simultaneously detected.

6. The method of claim 1, wherein the microorganism-concentrating film has a plurality of holes having a diameter of 0.1-5 mm.

7. The method of claim 1, wherein the microorganism-concentrating film is made of a material selected from the group consisting of PDMS (polydimethylsiloxane), a viscous polymer, an aluminum tape, rubber, latex, and a paste for screen printing.

8. The method of claim 1, wherein the microorganism-concentrating film is a film prepared by applying a screen-printing paste to the microorganism-capturing filtration membrane by a screen printing technique.

9. The method of claim 1, wherein a pore size of the microorganism-capturing filtration membrane ranges between 100 nm and 10 μm.

10. The method of claim 1, wherein the microorganism-capturing filtration membrane is made of a material selected from the group consisting of nitrocellulose, polycarbonate, nylon, polyester, cellulose acetate, polysulfone, and polyethersulfone.

11. The method of claim 1, wherein the selectively capturing step of the step (b) is performed by using vacuum, centrifugation, or absorption.

12. The method of claim 1, wherein determining of the step (c) is performed by a CCD camera or absorbance.

13. A device for detecting microorganisms, comprising:
a sample reaction unit comprising nanoparticles having immobilized thereon an antibody that binds specifically to the microorganisms to be detected;
a microorganism-concentrating film which receives a reaction solution from the sample reaction unit and concentrates the microorganisms to be detected;
a microorganism-capturing filtration membrane which captures and selectively separates the concentrated microorganisms that passed through the microorganism-concentrating film; and
a detection unit for determining the presence or concentration of the microorganisms.

14. The device of claim 13, wherein the nanoparticles are metal nanoparticles, quantum dot nanoparticles, or magnetic nanoparticles (MNPs).

15. The device of claim 13, wherein the microorganism-concentrating film is a film prepared by applying a screen-printing paste to the microorganism-capturing filtration membrane by a screen printing technique.

* * * * *